United States Patent
McDonagh et al.

(10) Patent No.: US 6,297,023 B1
(45) Date of Patent: Oct. 2, 2001

(54) ASSAY FOR PLASMINOGEN ACTIVATOR INHIBITOR-1 AND TISSUE PLASMINOGEN ACTIVATOR ACTIVITY

(75) Inventors: Jan McDonagh, Chestnut Hill; Myoung H. Lee, Brookline; Marcin J. Mankowski, Newton, all of MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 08/300,447

(22) Filed: Sep. 2, 1994

(51) Int. Cl.$^7$ ........................................... C12Q 1/56
(52) U.S. Cl. ........................ 435/13; 435/23; 435/184
(58) Field of Search ........................... 435/13, 23, 69.2, 435/184, 810, 975; 436/69, 166, 808

(56) References Cited

PUBLICATIONS

Zeffrene., The Study of Enzyme Mechanisms, John Wiley NY 1973 pp. 54–61.*
Segel I., Enzyme Kinetics, John Wiley NY 1975 pp. 107–111.*
Chmielewska, J., Determination of Tissue Plasminogen . . . Clin Chem 32: 482–485 (1986).*
Tze–Chein W, An Inhibitor of Plasminogen . . . J of Biol Chem 262 (8) 1987 pp. 3646–3653.*
Contant G., Determinationa of Plasminogen Activator . . . Thromb Res 56 1989 pp 377–386.*
Alessi M., Molecular Forms of Plasminogen . . . Thromb Res 62 1991 pp. 275–285.*
"COATEST® PAI Package Insert" Kabi Diagnostica, Taijegardagatan 3, S–43153 Sweden (1994).
"COA–SET® t–PA Package Insert" Kabi Diagnostica, Taijegardagatan 3, S–43153 Sweden (1994).
Chandler, Wayne L. et al., "Optimum conditions for the stabilization and measurement of tissue plasminogen activator activity in human plasma," *J. Lab Clin Med* 113(3):362–371 (1989).
Chandler, Wayne L. et al., "Standardization of Methods for Measuring Plasminogen Activator Inhibitor Activity in Human Plasma," *Clin. Chem.* 35(5):787–793 (1989).
Chmielewska, Joana and Wiman, Björn, "Determination of Tissue Plasminogen Activator and Its "Fast" Inhibitor in Plasma," *Clin. Chem.* 32:482–485 (1986).

* cited by examiner

*Primary Examiner*—Ralph Gitomer
(74) *Attorney, Agent, or Firm*—Hamilton, Brook, Smith & Reynolds, P.C.

(57) ABSTRACT

The invention is based upon the discovery that PAI-1 activity of a sample can be measured with sensitivity and correlation to in vivo activity without the use of standard curves. The assay determines the PAI-1 activity of a sample upon utilizing the second order rate equation for the reaction of PAI-1 and t-PA, as measured by their activities, in that sample.

16 Claims, No Drawings

ASSAY FOR PLASMINOGEN ACTIVATOR INHIBITOR-1 AND TISSUE PLASMINOGEN ACTIVATOR ACTIVITY

BACKGROUND OF THE INVENTION

Plasminogen activator inhibitor-1 is a natural inhibitor of tissue plasminogen activator. Deficiencies in plasminogen activator inhibitor-1 (PAI-1) results in delayed, or prolonged, bleeding. A high level of PAI-1 is indicative of heart disease. A reliable assay for the detection of low or high levels of PAI-1 activity is desirable.

PAI-1 has been expressed as arbitrary units (AU), wherein 1 AU of PAI-1 is the amount that inhibits 1 unit of tissue plasminogen activator (t-PA) under the conditions given. For example, in the assay as sold by Kabi the AU is measured during a 10 minute incubation of samples with standard t-PA at 37° C.

A current method (Coatest®, Kabi Diagnostics) for assaying PAI-1 activity in plasma or serum involves adding 40 U/ml t-PA, incubating the mixture for 10 minutes at room temperature and measuring the remaining t-PA activity in the sample. The remaining t-PA activity is converted to PAI-1 activity (AU/ml) using a standard curve which is generated by adding 40 U/ml t-PA in PAI-1 depleted plasma (0 AU/ml PAI-1) and no t-PA added (40 AU/ml PAI-1). Chmielewska et al., *Clinical Chemistry*, 32(3):482–485 (1986), incorporated herein by reference.

This prior art method has several drawbacks. The sensitivity or experimental error of the assay near the low and high ends of the range, in this case, 0 and 40+AU/ml (dictated by the amount of t-PA added to the sample), can be poor. For example, samples containing higher activity than 40 AU/ml PAI-1 are not detected, requiring sample dilution or increased amounts of t-PA to be added to the assay with the development of new standard curves.

PAI-1, t-PA and the complex of PAI-1·t-PA are under equilibrium in vivo, with secretion and clearance of t-PA and PAI-1, and the inhibition reaction. Since this quilibrium is not the same in a plasma sample, the prior art assay may not determine the PAI-1 activity in vivo under physiological conditions. Thus, PAI-1 activity determined in a plasma sample can be lower than that in vivo, depending upon the original t-PA activity in vivo.

This prior art assay has the further drawback in that the values produced are highly dependent upon the standard curve and the accuracy of the t-PA activity used in the assays, requiring that new standard curves be generated with new samples.

Accordingly, an assay which can be employed to accurately measure PAI-1 and t-PA activity in vivo as well as in vitro, and the half-life of t-PA activity in a sample is desirable.

SUMMARY OF THE INVENTION

The invention relates to a method for assaying the PAI-1 activity and/or t-PA activity in a sample comprising measuring the activity of t-PA in the sample as a function of time and obtaining the PAI-1 and/or the t-PA activity from the second order rate equation, described below. The half-life of t-PA activity in an individual can also be determined from the assay. The invention includes methods of assaying or determining the PAI-1 and t-PA activities and the half-life of t-PA activity in a sample and kits therefor.

The invention provides an accurate assay for the determination of PAI-1 and t-PA activity in a sample which is not encumbered by the preparation of a new standard curve for t-PA activity with a new sample.

In one embodiment the invention includes a method for assaying the PAI-1 activity and/or t-PA activity in a sample wherein the sample is a body fluid comprising the steps of:

(a) adding tissue plasminogen activator to the sample;
(b) acidifying the sample;
(c) contacting a first preselected amount of the sample with plasminogen, thereby obtaining a mixture:
(d) maintaining the mixture under conditions sufficient to permit the t-PA-catalyzed conversion of plasminogen to plasmin;
(e) measuring the amount of plasmin formed, thereby measuring the activity of t-PA, (tPA) at a first time, t;
(f) repeating steps (c) through (d) at least at two different times, t
(g) employing the (tPA) at the first and second times, t, in the formula:

$$kt = -1/((PAI)_0 - (tPA)_0) \ln\{(tPA)_0[(PAI)_0 - (tPA)_{0+(tPA)}]\}/(PAI)_0(tPA)$$

wherein $(PAI)_0$ is the initial activity of PAI-1 at time zero;
$(tPA)_0$ is the initial activity of t-PA at time zero; and
$(tPA)$ is the activity of t-PA at time t;
k is the second order rate constant for the reaction:

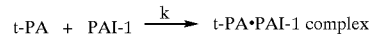

at assay conditions; and
(h) obtaining the values of $(PAI-1)_0$ and/or $(tPA)_0$ therefrom.

DETAILED DESCRIPTION OF THE INVENTION

The assay of the invention measures the activity of t-PA in a sample as a function of time and then calculates the activities of PAI-1 and/or t-PA at time zero, employing the second order reaction mechanism of PAI-1 and t-PA. The reaction is depicted by the formula.

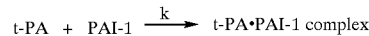

Wherein k is the second order rate constant for the reaction. The second order rate constant can be calculated by equation I:

$$-d(t\text{-}PA)/dt = k(t\text{-}PA)(PAI) \text{TM I}$$

The second order rate constant (k) can be determined by plotting a series of pseudo-first-order rate constants of k (PAI-1) according to equation I. The second order rate constant will vary as a function of temperature, as is known in the art. For example, at room temperature, the second order rate constant, k, was determined by plotting a series of pseudo-first-order rate constant of k(PAI), approximately $-0.014$ $U^{-1}min^{-1}$ under the conditions where PAI-1 is expressed in U/ml and t-PA activity is expressed as A405 (O.D.), as described below in the exemplification.

With this calculation, the PAI-1 activity at time zero and t-PA activity at time zero can be determined employing the above rate equation (II). The second order rate equation (II) for the reaction is:

$$kt = -1/((PAI)_0 - (tPA)_0) \ln\{(tPA)_0[(PAI)_0 - (tPA)_0 + (tPA)]\}/(PAI)_0(tPA) \text{TM II}$$

wherein t=time; $(PAI)_0$ is the initial activity of PAI-1 at time zero;

$(tPA)_0$ is the initial activity of t-PA at time zero; and $(tPA)$ is the activity of t-PA at time t.

PAI-1 activity is measured as U/ml (units per milliliter, in contrast to "arbitrary units" discussed above). 1 U/ml of PAI-1 is the amount of PAI-1 required to inhibit 1 U/ml of t-PA. Generally 1 U/ml as determined herein, is the same or similar to 1 AU/ml. Upon determining the second order rate constant for the assay conditions to be employed, generation of a new standard curve for each assay can be avoided in the present assay.

Employing the assay, one can determine the activity of t-PA and/or PAI-1 at time zero from the rate equation (II). The assay can also be advantageously employed to measure the half-life of endogenous t-PA activity or exogenously added t-PA activity. In this embodiment, the time, t, where $(t\text{-}PA)$ is $\frac{1}{2}$ $(t\text{-}PA)_0$, is calculated from the rate equation (II).

Samples which can be assayed for PAI-1 activity according to the claimed method include body fluids, such as blood, plasma, serum, urine or saliva. For example, freshly drawn blood plasma or serum can be assayed.

Where the sample to be assayed is blood, it is advantageous to centrifuge the sample, as is known in the art.

Preferably, the sample is acidified with a suitable buffer to achieve a pH between about 3.5 to about 4.5, most preferably about 4, with the appropriate ionic strength. An appropriate ionic strength can be between about 0.2 M to about 0.5 M, such as about 0.3 M. Acidification of the sample advantageously results in the inhibition of the t-PA-PAI-1 reaction.

Preferred buffers can include those which will not cause precipitation, such as protein precipitation, and will result in the acidification of the sample to the desired pH. An example of a suitable buffer is sodium acetate.

Optionally, t-PA is added to the sample. An example of where t-PA addition can be avoided is where the patient has, or is expected to have, high t-PA activity, such as, where the blood sample is drawn after venous occlusion. t-PA activity in these samples is generally high. In this case, the endogenous t-PA activity is measured as a function of time. t-PA can be added to the sample advantageously where the endogenous t-PA activity is not at a sufficient level to permit an accurate measurement of decrease in the activity over time. In one embodiment, the t-PA is added to the container which will receive the sample. Generally, at least about 2 U/ml t-PA is added to the sample. Preferably, about 2 to about 7 U/ml t-PA is added to the sample. About 5 U/ml t-PA is suitable. One advantage of this method is that no accurate measurement of added t-PA is required.

Optionally, a standard t-PA sample is run simultaneously. In this embodiment, the endogenous t-PA activity of the sample in vivo can be determined accurately by converting the measured t-PA activity of the sample at zero time to U/ml, employing the assay measurement for standard t-PA as the conversion factor.

The assay can be conducted at any temperature which permits the reaction between t-PA and PAI-1. The temperatures at which the sample is prepared and t-PA measured may be the same or different. Preferably the temperature(s) are less than that at which protein precipitates in the sample (about 42° C.) and greater than about 15° C. It can be convenient to prepare the sample at about room temperature. t-PA activity can be measured at a temperature below which t-PA is inactivated. A suitable temperature for use with a microplate reader to measure t-PA activity, such as described below, is about 37° C.

The assay relies upon the measurement of t-PA activity as a function of time. A variety of known methods for measuring t-PA activity can be employed. Suitable methods are described in Chandler et al., *J. Lab. Clin. Med.*, 113(3):362–371 (1989) and Chandler et al., *Clinical Chem.* 35(5):787–793 (1989), incorporated herein by reference. Preferably, the assay is a coupled assay. Also preferred is the use of a chromogenic substrate in the assay. In one embodiment, the activity can be measured in a coupled assay with a plasminogen, such as glu-plasminogen, and a chromogenic substrate, such as H-D-Val-Leu-Lys-para-nitroaniline (S-2251), H-Glu-Phe-Lys-para-nitroanaline (S-2403), H-D-Val-Phe-Lys-para-nitroanaline (S-2390), available from chomogencs. Plasmin is generated from the reaction of the plasminogen present in the sample and t-PA. The plasmin thereby formed catalyzes the chromogenic substrate (e.g., S-2251) which results in increase of absorbance (in the case of S-2251, at 405 nm). In such an assay, the t-PA activity is proportional to the measured absorbance at 405 nm (A405 (OD)).

The activity of t-PA is measured at three or more distinct time intervals, preferably at five or more distinct time intervals. The time period between time zero and the last measurement is preferably equal to or less than about 20 minutes. The minimal preferred time intervals between measurements is about 30 seconds. Suitable time intervals which can be employed are in the range of about 30 seconds to about 2 minutes.

A computer program which calculates the values set forth above, employing the formulae provided, can be generated according to means known in the art. Such a program can facilitate evaluating the assay. Alternatively, a chart or charts can be generated or provided to calculate one or more of the variables k, $(PAI)_0$ or $(t\text{-}PA)_0$ or the half lives of PAI-1 or t-PA.

The values of the PAI-1 activity at time zero can then be compared to the PAI-1 activities considered to be in the normal range (6.0±3.8 AU/ml). Values that are less than about 1 AU/ml are indicative of PAI-1 deficiency. Values that are greater than about 20 AU/ml can be indicative of high PAI-1 activity. A half-life of t-PA activity of greater than about 15 minutes is also indicative of PAI-1 deficiency. Average resting t-PA activity in plasma in health individuals has been reported as 1.59 U/ml (Chandler et al., supra.).

The invention further relates to kits which can be employed in the assay. The kits of the invention include one or more of the following components: t-PA; a buffer, such as sodium acetate, as described above; plasminogen, preferably glu-plasminogen; a substrate for assessing t-PA activity, such as a chromogenic substrate such as S-2251; and a fibrinogen, such as CNBr-cleaved fibrinogen or a fibrin. The kit also includes an insert, which instructs as to the methodology and evaluation of the assay. For example, a diskette which contains a computer program for calculating one or more of k, $(PAI)_0$ or $(t\text{-}PA)_0$ or the half-life of t-PA activity employing the equation (I) and/or rate equation (II) set forth above. Alternatively, the insert would include a description of the equation (I) and rate equation (II) for evaluating the data as described herein.

The invention will now be described more specifically by the exemplification.

EXAMPLE

To a plasma sample, approximately 5 U/ml of t-PA was added to the sample. Every minute, 2 volumes of blood were mixed with one volume of 1 M sodium acetate buffer, pH 3.9. Ten samples were collected over ten minutes. The samples were centrifuged, thereby preparing acidified plasma. The plasma was diluted 20 times with water. Eighty microliters of diluted plasma were assayed with 80 microliters of assay mixture containing glu-plasminogen and S-2251. The reaction was initiated with 40 microliters of CNBr cleaved fibrinogen (FCB). The final concentration of glu-plasminogen, S-2251 and FCB were 0.05 mg/ml, 0.6 mM and 0.15 mg/ml, respectively. The assays were done on microplates by keeping the plate at 37° C. for about 2.5 hours. Absorbance at 405 nm (A405 (O.D.)) was measured on a microplate reader. The A405 (O.D.) values were plotted as a function of time.

PAI-1 activity at time zero was calculated in four plasma samples, giving values of 5.6, 8.7, 14.9 and 22.9 U/ml, k=−0.0138.

Plasma and serum samples can also be assayed according to the method described above. Preferably, the acidification of the samples should be conducted at approximately 1:1 ratio by volume of sample to buffer.

Equivalents

Those skilled in the art will recognize, or be able to ascertain using no more than routine experimentation, many equivalents to the specific embodiments of the invention described specifically herein. Such equivalents are intended to be encompassed in the scope of the claims.

What is claimed is:

1. A method for obtaining an initial activity of plasminogen activator inhibitor-1, an initial activity of tissue plasminogen activator, or a half-life of tissue plasminogen activity in a sample comprising the steps of:

(a) measuring activity of tissue plasminogen activator in the sample as a function of time; and (b) obtaining a value of $(PAI)_0$, $(t\text{-}PA)_0$ or $\frac{1}{2}(t\text{-}PA)_0$; from formula:

$$kt=-1/((PAI)_0-(tPA)_0)\ln\{(tPA)_0[(PAI)_0-(tPA)_0+(tPA)]\}/(PAI)_0(tPA)$$

wherein $(PAI)_0$ is the initial activity of plasminogen activator inhibitor-1 in the sample;

$(tPA)_0$ is the initial activity of tissue plasminogen activator in the sample;

(tPA) is an activity of tissue plasminogen activator at time t; and the half-life of tissue plasminogen activator in the sample is a value for t wherein (tPA) is $\frac{1}{2}(t\text{-}PA)_0$;

k is a second order rate constant for a reaction:

2. The method of claim 1 wherein the sample is a body fluid.

3. The method of claim 2 wherein the sample is blood, plasma or serum.

4. The method of claim 2 further comprising adding tissue plasminogen activator to the sample.

5. The method of claim 2 further comprising acidifying the sample, thereby obtaining an acidified sample.

6. The method of claim 5 wherein the sample is acidified with a sodium acetate buffer.

7. The method of claim 5 wherein the acidified sample has a pH between about 3.5 to about 4.5.

8. The method of claim 7 wherein the pH of the acidified sample is about 4.

9. The method of claim 5 wherein the sample is maintained at about room temperature.

10. The method of claim 5 wherein the activity of tissue plasminogen activator in step (a) is measured in a coupled assay.

11. The method of claim 5 wherein the activity of tissue plasminogen activator in step (a) is measured by the steps:

(a) contacting a preselected amount of the sample with a preselected amount of plasminogen, thereby obtaining a mixture:

(b) maintaining the mixture under conditions sufficient to permit tissue plasminogen activator-catalyzed conversion of plasminogen to plasmin; and (c) measuring an amount of plasmin formed.

12. The method of claim 11 wherein the amount of plasmin formed is measured by contacting the plasmin with a chromogenic substrate and measuring an increase in absorbance of the sample.

13. The method of claim 12 wherein the plasminogen is glu plasminogen.

14. The method of claim 5 wherein the activity of tissue plasminogen activator in step (a) is measured at three or more distinct intervals.

15. The method of claim 14 wherein the activity of tissue plasminogen activator in step (a) is measured at five or more distinct intervals.

16. A method for obtaining an initial activity of plasminogen activator inhibitor-1, an initial activity of tissue plasminogen activator, or a half-life of tissue plasminogen activity in a sample, wherein the sample is a body fluid, comprising the steps of:

(a) adding tissue plasminogen activator to the sample;

(b) acidifying the sample;

(c) contacting a first preselected amount of the sample with plasminogen, thereby obtaining a mixture:

(d) maintaining the mixture under conditions sufficient to permit tissue plasminogen activator-catalyzed conversion of plasminogen to plasmin;

(e) measuring the plasmin formed in step (d), thereby measuring activity of tissue plasminogen activator at a first time, t;

(f) repeating steps (c) through (d) at least at two different times, t;

(g) obtaining a value of $(PAI)_0$, $(tPA)_0$ or $\frac{1}{2}(t\text{-}PA)_0$ from a formula:

$$kt=-1/((PAI)_0-(tPA)_0)\ln\{(tPA)_0[(PAI)_0-(tPA)_0+(tPA)]\}/(PAI)_0(tPA)$$

wherein $(PAI)_0$ is the initial activity of plasminogen activator inhibitor-1 in the sample;

$(tPA)_0$ is the initial activity of tissue plasminogen activator in the sample;

(tPA) is an activity of tissue plasminogen activator at time t; and the half-life of tissue plasminogen activator in the sample is the value for t wherein (tPA) is $\frac{1}{2}(t\text{-}PA)_0$;

k is a second order rate constant for a reaction:

* * * * *